US008166821B2

(12) United States Patent
Killian et al.

(10) Patent No.: US 8,166,821 B2
(45) Date of Patent: May 1, 2012

(54) NON-DESTRUCTIVE TEST EVALUATION OF WELDED CLADDINGS ON RODS OF HYDRAULIC CYLINDERS USED FOR SALTWATER, BRACKISH AND FRESHWATER APPLICATIONS

(75) Inventors: Michael Killian, Troy, MI (US); Aquil Ahmad, West Bloomfield, MI (US)

(73) Assignee: Eaton Corporation, Cleveland, OH (US)

( * ) Notice: Subject to any disclaimer, the term of this patent is extended or adjusted under 35 U.S.C. 154(b) by 418 days.

(21) Appl. No.: 12/493,671

(22) Filed: Jun. 29, 2009

(65) Prior Publication Data

US 2010/0008462 A1 Jan. 14, 2010

Related U.S. Application Data

(60) Provisional application No. 61/080,402, filed on Jul. 14, 2008.

(51) Int. Cl.
*G01N 29/26* (2006.01)
(52) U.S. Cl. ............................................ 73/601; 73/602
(58) Field of Classification Search .................... 73/601, 73/622, 637, 865.8, 602; 376/245, 252, 258; 324/237, 240, 243
See application file for complete search history.

(56) References Cited

U.S. PATENT DOCUMENTS

| 3,693,975 A | | 9/1972 | Ruggiero | |
|---|---|---|---|---|
| 4,162,758 A | * | 7/1979 | Mikarai | ......................... 228/131 |
| 4,608,534 A | * | 8/1986 | Cecco et al. | .................. 324/238 |
| 4,673,879 A | * | 6/1987 | Harris et al. | ................... 324/240 |
| 4,755,753 A | * | 7/1988 | Chern | .......................... 324/237 |
| 5,418,823 A | * | 5/1995 | Kervinen et al. | .............. 376/245 |
| 5,926,020 A | * | 7/1999 | Samson | ........................ 324/238 |
| 5,963,030 A | * | 10/1999 | Stark | .............................. 324/229 |
| 6,165,542 A | * | 12/2000 | Jaworowski et al. | ........... 427/10 |
| 7,942,307 B2 | * | 5/2011 | Greenwall | ................... 228/17.7 |
| 7,982,459 B2 | * | 7/2011 | Killian et al. | ................. 324/240 |
| 2002/0194916 A1 | * | 12/2002 | Yamada et al. | ................. 73/627 |
| 2006/0055401 A1 | | 3/2006 | Kuljis et al. | |
| 2008/0121041 A1 | | 5/2008 | Smith et al. | |

FOREIGN PATENT DOCUMENTS

| DE | 29517292 U1 | 12/1995 |
|---|---|---|
| GB | 2273782 A | 6/1994 |

OTHER PUBLICATIONS

PCT International Search Report (Form PCT/ISA/210) and written opinion of the ISA (Form PCT/ISA/237)—13 total pages.

* cited by examiner

*Primary Examiner* — J M Saint Surin
(74) *Attorney, Agent, or Firm* — Quinn Law Group, PLLC

(57) ABSTRACT

A method of maintaining a rod of a hydraulic cylinder for a motion compensation system of an offshore platform includes non-destructive testing of a metallic cladding deposited onto the rod. An inspection crawler includes a visual inspection device, an eddy current inspection device and an ultrasonic inspection device. The method includes rotating the visual inspection device, the eddy current inspection device and the ultrasonic inspection device around a circumference of the rod while moving the inspection crawler along a longitudinal axis of the rod to simultaneously collect data related to the metallic cladding from the visual inspection device, the eddy current inspection device and the ultrasonic inspection device. The data is analyzed to detect any discontinuities, i.e., defects, in the metallic cladding.

19 Claims, 2 Drawing Sheets

NON-DESTRUCTIVE TEST EVALUATION OF WELDED CLADDINGS ON RODS OF HYDRAULIC CYLINDERS USED FOR SALTWATER, BRACKISH AND FRESHWATER APPLICATIONS

CROSS-REFERENCE TO RELATED APPLICATIONS

This application claims the benefit of U.S. Provisional Patent Application Ser. No. 61/080,402, filed on Jul. 14, 2008, the disclosure of which is hereby incorporated by reference.

TECHNICAL FIELD

The present invention generally relates to a method of maintaining a rod of a hydraulic cylinder, and more specifically to a non-destructive method of inspecting a metallic cladding welded to a rod of the hydraulic cylinder.

BACKGROUND OF THE INVENTION

Offshore platforms, such as offshore oil rigs, include a motion compensation system that utilizes large hydraulic cylinders to stabilize the platforms. The hydraulic cylinders include rods, which are susceptible to corrosion caused by exposure to the elements. These large hydraulic cylinders also are used in civil engineering and hydropower applications including locks, dams and bridges.

The rods of the hydraulic cylinders may include solid or tubular rods manufactured from an austenitic nickel-chromium based alloy or a duplex stainless steel. However, the rods manufactured from the nickel-chromium based alloy or the duplex stainless steel are expensive. An alternative includes constructing the rods with a metallic cladding welded to an exterior surface of a rod machined from conventional steel. The metallic cladding protects the rods from corrosion, provides wear resistance and is a lower cost alternative to the solid or tubular rods manufactured entirely from the nickel-chromium based alloy or the duplex stainless steel.

The rods having the metallic cladding are typically manufactured from SAE 4130 steel. The protective metallic cladding may include a stainless steel material, a nickel based material or a cobalt based material. The metallic claddings may be deposited onto the rod by one of a number of fusion welding processes, including a laser welding process, a Plasma Transferred Arc (PTA) welding process, a Submerged Arc Welding (SAW) process, a Gas Tungsten Arc Welding (GTAW) process, a Gas Metal Arc Welding (GMAW) process, and a Shielded Metal Arc Welding (SMAW) process. Common to all of the above welding processes is the melting of the substrate, i.e., the outer surface of the rod, and the deposition of the metallic cladding material.

If the metallic cladding is not properly deposited onto the rod, then the metallic cladding may include a discontinuity in the metallic cladding, i.e., a defect in the metallic cladding. The discontinuities of the metallic cladding may include porosity in the metallic cladding, cluster porosity in the metallic cladding, cracks in the metallic cladding, shrink of the metallic cladding, incomplete fusion of the metallic cladding onto the rod, excessive penetration (high dilution) of the metallic cladding onto the rod or disbanding of the metallic cladding from the rod.

Additionally, discontinuities in the metallic cladding may form during use of the hydraulic rod in service. For example, small surface and subsurface discontinuities that would be barely noticeable at the time of weld cladding, can propagate due to high bending stresses, impacts and fatigue loads. Very high reversed bending loads can initiate and propagate fatigue cracks in the metallic cladding from the most minute stress risers like oxidized grain boundaries.

The service life of the rod is further complicated by the harsh marine environment in which the hydraulic cylinders must operate. Water borne debris, including ice, may impact the rods. Splashing water continually replenishes oxygen within surface opening discontinuities. Propagating discontinuities, such as pores and cracks in the metallic cladding, may link up to provide a pathway to the bondline between the surface of the rod and the metallic cladding. Once water reaches the steel of the rod at the bondline, corrosion occurs rapidly. Bondline corrosion eventually causes the metallic cladding to spall off, leaving the steel of the rod exposed and unprotected. Eventually, the propagation of the discontinuities in the metallic cladding, corrosion of the steel rod and spalling of the metallic cladding critically damage the rod, and may cut or tear seals and may result in the failure of the cylinder.

SUMMARY OF THE INVENTION

A method of maintaining a rod of a hydraulic cylinder is disclosed. The rod includes a metallic cladding welded thereto. The method utilizes an inspection crawler, which includes a visual inspection device, an eddy current inspection device and an ultrasonic inspection device. The method includes mounting the inspection crawler to the rod; positioning the inspection crawler at a start location; activating the visual inspection device, the eddy current inspection device and the ultrasonic inspection device to collect data related to the metallic cladding; moving the inspection crawler linearly along a longitudinal axis of the rod from the start location to an end location while rotating the visual inspection device, the eddy current inspection device and the ultrasonic inspection device around a circumference of the rod to simultaneously collect data related to the metallic cladding from the visual inspection device, the eddy current inspection device and the ultrasonic inspection device along the entire length and circumference of the rod between the start location and the end location; and analyzing the data collected from the visual inspection device, the eddy current inspection device and the ultrasonic inspection device to identify a discontinuity in the metallic cladding.

A system for inspecting a metallic cladding on a rod of a hydraulic cylinder is also disclosed. The system includes an inspection crawler configured for moveable attachment to the rod. A visual inspection device is mounted to the inspection crawler, and is configured to visually inspect the metallic cladding on the rod. An eddy current inspection device is mounted to the inspection crawler. The eddy current inspection device is configured to detect change in one of a magnetic permeability or an electrical conductivity of the metallic cladding on the rod. An ultrasonic inspection device is also mounted to the inspection crawler. The ultrasonic inspection device is configured to detect change in sound waves propagated through the metallic cladding on the rod. The visual inspection device, the eddy current inspection device and the ultrasonic inspection device are configured for rotation about a circumference of the rod, while the inspection crawler moves linearly along a longitudinal axis of the rod to simultaneously collect data related to the metallic cladding from the visual inspection device, the eddy current inspection device and the ultrasonic inspection device along a length and the circumference of the rod.

A method of inspecting a metallic cladding welded to a rod of a hydraulic cylinder is also disclosed. The method includes positioning an eddy current inspection device adjacent the metallic cladding of the rod, activating the eddy current inspection device to collect data related to the metallic cladding, and analyzing the data collected from the eddy current inspection device to identify a discontinuity in the metallic cladding.

Accordingly, the method and system for maintaining the rod of the hydraulic cylinder allows for the non-destructive testing or inspection of the metallic cladding on the rod to detect any discontinuities in the metallic cladding that may require repair. The metallic cladding may be inspected on-site at an offshore platform on a regular basis to monitor the wear of the metallic cladding over time and detect any discontinuities that develop over time. Early detection of any discontinuities in the metallic cladding permit a timely response to correct the discovered discontinuity in the metallic cladding and maintain the proper operation of the hydraulic cylinder. Additionally, the use of the eddy current inspection device provides a more accurate and detailed inspection of the metallic cladding than existing liquid penetration inspections currently utilized.

The above features and advantages and other features and advantages of the present invention are readily apparent from the following detailed description of the best modes for carrying out the invention when taken in connection with the accompanying drawings.

DESCRIPTION OF THE PREFERRED EMBODIMENTS

Referring to the Figures, wherein like numerals indicate like parts throughout the several views, an inspection system is shown generally at 20. The inspection system 20 is for inspecting a metallic cladding 22 on a rod 24 of a hydraulic cylinder 26. The metallic cladding 22 is shown in detail in FIG. 2. The hydraulic cylinder 26 is utilized for a motion compensation system of an offshore platform, such as an oil rig or the like. The metallic cladding 22 protects the rod 24 from the elements to prevent corrosion of the rod 24.

The rod 24 may include and be manufactured from SAE 4130 steel. However, it should be appreciated that the rod 24 may include and be manufactured from some other grade of steel, and may include and be manufactured from a metal other than steel. The protective metallic cladding 22 may include, but is not limited to, one of a stainless steel material, a nickel based material or a cobalt based material. It should be appreciated that the metallic cladding 22 may include some other material capable of being disposed onto the rod 24 and protecting the rod 24 from the environment to prevent corrosion of the rod 24.

The metallic cladding 22 may be deposited onto the rod 24 by a fusion welding process, such as but not limited to, a laser welding process, a Plasma Transferred Arc (PTA) welding process, a Submerged Arc Welding (SAW) process, a Gas Tungsten Arc Welding (GTAW) process, a Gas Metal Arc Welding (GMAW) process, and a Shielded Metal Arc Welding (SMAW) process. It should be appreciated that the metallic cladding 22 may be deposited onto and/or bonded to the rod 24 by some other process not described herein.

Figure 2:
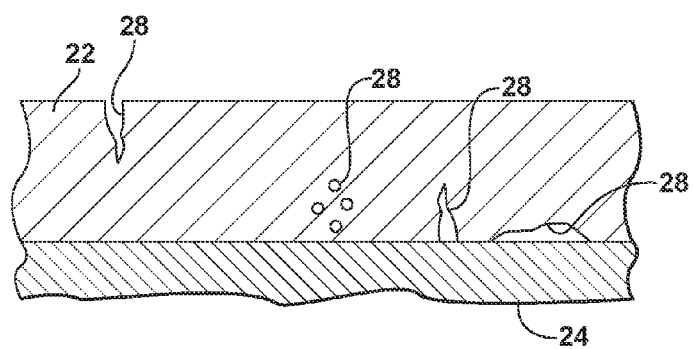
FIG. 2 is an enlarged schematic fragmentary cross sectional view of a metallic cladding on the rod showing discontinuities therein.

Referring to FIG. 2, if the metallic cladding 22 is not properly deposited onto the rod 24, then the metallic cladding 22 may include a discontinuity 28, i.e., a defect in the metallic cladding 22. The discontinuity 28 of the metallic cladding 22 may include one of porosity in the metallic cladding 22, a cluster porosity in the metallic cladding 22, a crack in the metallic cladding 22, shrinkage of the metallic cladding 22, incomplete fusion of the metallic cladding 22 onto the rod 24, excessive penetration (high dilution) of the metallic cladding 22 into the rod 24 and disbanding of the metallic cladding 22 from the rod 24.

Additionally, a discontinuity 28 in the metallic cladding 22 may form during use of the hydraulic rod 24 in service. For example, small surface and subsurface discontinuities 28 that would be virtually undetectable at the time of deposition of the metallic cladding 22 onto the rod 24, may propagate due to high bending stresses, impact loads and fatigue loads. Furthermore, very high reverse bending loads may initiate and propagate fatigue cracks in the metallic cladding 22 from the most minute stress risers like oxidized grain boundaries.

Figure 1:
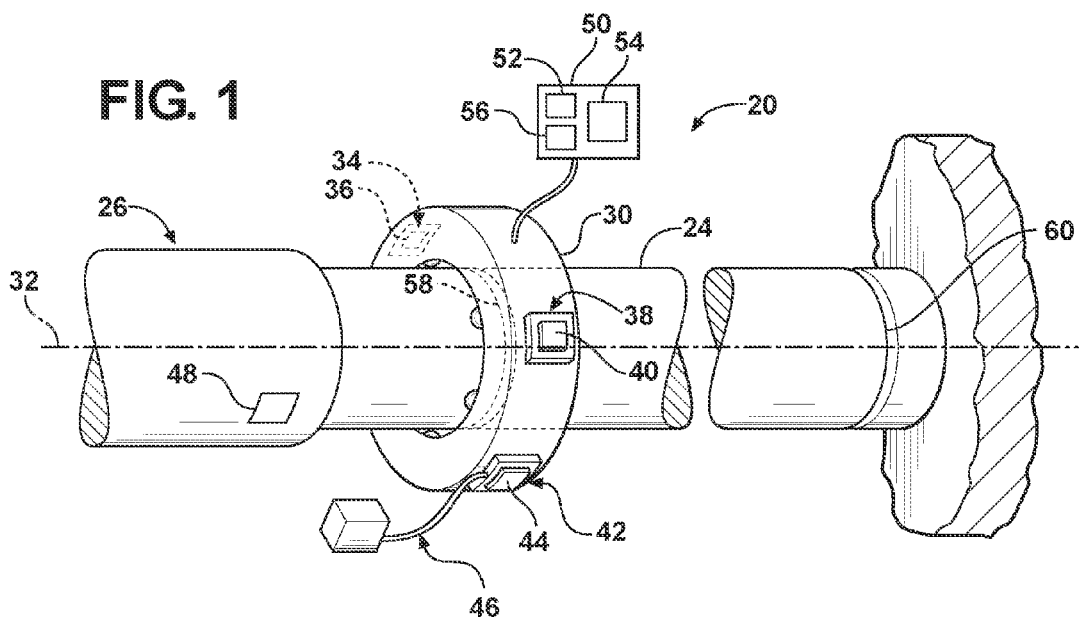
FIG. 1 is a schematic partially cut-away perspective view of a hydraulic cylinder and a system for inspecting a rod of the hydraulic cylinder.

Referring to FIG. 1, the inspection system 20 includes an inspection crawler 30 configured for moveable attachment to the rod 24. The inspection crawler 30 may be configured in any suitable manner to enable the inspection crawler 30 to grasp the rod 24 and move a length along a longitudinal axis 32 of the rod 24. The inspection crawler 30 may include a translation device capable of self propelling the inspection crawler 30 along the length of the rod 24. Alternatively, the inspection system 20 may include a remotely located translation device configured to draw, i.e., pull, the inspection crawler 30 along the length of the rod 24.

The inspection crawler 30 includes a visual inspection device 34 mounted to the inspection crawler 30. The visual inspection device 34 is configured for visual inspection of the metallic cladding 22 on the rod 24. The visual inspection device 34 may include a camera 36. More specifically, the camera 36 may include a digital camera, such as, but not limited to, a Charge Coupled Device (CCD) camera or a Complimentary Metal Oxide Semiconductor (CMOS) camera. The camera 36, once actuated, videos the metallic cladding 22 of the rod 24. The camera 36 is preferably capable of magnification of the surface of the metallic cladding 22 to provide a close examination of the metallic surface. An operator is able to view the video to visually inspect the metallic cladding 22 for discontinuities 28. Accordingly, the visual inspection device 34 is capable of detecting a discontinuity 28 in the surface of the metallic cladding 22.

The inspection crawler 30 further includes an eddy current inspection device 38 mounted to the inspection crawler 30. The eddy current inspection device 38 includes a current transducer 40, and is configured for detecting change in one of a magnetic permeability or an electrical conductivity of the metallic cladding 22 on the rod 24.

The eddy current inspection device 38 is sensitive to changes in the geometry of the rod 24, electric conductivity of the metallic cladding 22 on the rod 24 and magnetic permeability of the metallic cladding 22 on the rod 24. For ferrous work pieces, the predominant change that is measured is usually a variation in the magnetic permeability. With non-ferrous work pieces, the predominant change that is measured is usually a variation in the electrical conductivity.

The eddy current inspection device 38 is well suited for detecting discontinuities 28 near the surface of the metallic cladding 22. Depth of penetration of the interrogating magnetic field of the eddy current inspection device 38 into the rod 24 is determined by the frequency of the driving voltage. Reaching the bondline between the rod 24 and the metallic cladding 22, which is typically at a depth of 0.050 inches, is within the capabilities of the eddy current inspection device 38. The eddy current inspection device 38 may include differentially connected hall devices, which make the eddy current inspection device 38 very sensitive to cracks in the metallic cladding 22. The eddy current inspection device 38 may utilize multiple frequencies and scanning array transducers to reveal numerous subsurface cracks in the metallic cladding 22 of the rod 24.

The inspection crawler 30 further includes an ultrasonic inspection device 42 mounted to the inspection crawler 30. The ultrasonic inspection device 42 includes an ultrasonic transducer 44, and is configured for detecting a change in sound waves propagated through the metallic cladding 22 on the rod 24. Ultrasonic tests are based upon the reflection of sound waves caused by changes in the propagating velocities as different media, i.e., discontinuities 28, are encountered by the sound waves. As ultrasonic sound wave propagates through the metallic cladding 22, no reflection occurs until the sound wave reaches the bondline between the rod 24 and the metallic cladding 22. However, if the metallic cladding 22 is cracked, the ultrasonic sound wave propagates through the steel but is reflected at the interface between the steel and the crack filled with air, gas or a vacuum.

A conventional Ultrasonic Testing (UT) Amplitude Scan (A-scan), may readily find a discontinuity 28 measuring 0.030 inches or deeper in ferrous and non-ferrous work pieces. Ultrasonic inspection is well suited for identification of subsurface discontinuities 28. Ultrasonic testing becomes more difficult when the discontinuity 28 is located very near the surface of the metallic cladding 22. To detect any discontinuity 28 located near the surface of the metallic cladding 22, the ultrasonic inspection device 42 may shift from the Amplitude Scan with longitudinal sound waves to one of an angle beam shear sound waves or a surface sound wave that travels along the surface of the metallic cladding 22 to a depth of one sound wave. The ultrasonic inspection device 42 may include a phased array, multiple channel inspection capability. The transducer array enables multiple beam angles to be evaluated during a single inspection.

The ultrasonic inspection device 42 may include a water injection system 46. The water injection system 46 connects a pressurized water source to the ultrasonic transducer 44. The water injections system supplies a stream of water onto the metallic cladding 22 of the rod 24. The ultrasonic sound waves are transmitted through the water stream to the rod 24. The water stream functions as a continually applied couplant to transmit the ultra sonic sound waves to the rod 24. The ultrasonic testing device may also be utilized to measure the thickness of the metallic cladding 22 to determine loss of material due to wear, spalling, impacts, dents and corrosion.

An alternative to the water injection system 46 includes one of the rod 24 and the inspection crawler 30 having an Electro Magnetic Acoustic Transducer (EMAT) 48. The EMAT 48 may be attached to the inspection crawler 30 or may be attached to the hydraulic cylinder 26. The EMAT 48 provides an electromagnetic pulse that is converted to an ultrasonic sound wave within the rod 24. The EMAT 48 does not require a couplant, such as water, and therefore does not require the use of the water injection system 46.

The inspection system 20 further includes a computer 50. The computer 50 includes a processor 52, a memory 54 and software 56 for operating the visual inspection device 34, the eddy current inspection device 38 and the ultrasonic inspection device 42. The computer 50 may be attached to the inspection crawler 30, or be remotely located from the inspection crawler 30 and in communication with the inspection crawler 30. If located remotely from the inspection crawler 30, the computer 50 may be in communication with the inspection crawler 30 through, for example, a wired communication network or wireless communication network. The memory 54 is configured for storing data collected from the visual inspection device 34, the eddy current inspection device 38 and the ultrasonic inspection device 42. The memory 54 may include any suitable type of memory 54 known for use with computers. It should be appreciated that the computer 50 includes all necessary components and/or equipment needed to operate the inspection system 20, such as a monitor, a keyboard, a mouse, a printer, etc.

The rod 24 includes a first indexing mechanism 58 and a second indexing mechanism 60. The first indexing mechanism 58 is located at one end of the rod 24, and the second indexing mechanism 60 is located at an opposite end of the rod 24. The first indexing mechanism 58 identifies a start location for the inspection crawler 30 to begin inspection of the metallic cladding 22, and the second indexing mechanism 60 identifies an end location for the inspection crawler 30 to end inspection of the metallic cladding 22. The first indexing mechanism 58 and the second indexing mechanism 60 may include, but is not limited to, a projection or a recess in the rod 24 that is identifiably or capable of being sensed by the inspection crawler 30. Preferably, the inspection process always begins at the start location and ends at the end location. However, it does not matter which end of the rod 24 the start location and the end location or located.

The visual inspection device 34, the eddy current inspection device 38 and the ultrasonic inspection device 42 are configured for rotation about a circumference of the rod 24 while the inspection crawler 30 moves linearly along a longitudinal axis 32 of the rod 24. Accordingly, the visual inspection device 34, the eddy current inspection device 38 and the ultrasonic inspection device 42 simultaneously collect data related to the metallic cladding 22 from the visual inspection device 34, the eddy current inspection device 38 and the ultrasonic inspection device 42, along a length and the circumference of the rod 24. In this fashion, all of the data from the different inspection devices is collected by the inspection crawler 30 at the same time.

The inspection crawler 30 may further include a linear and a rotational encoder to monitor movement of the inspection crawler 30 along the rod 24 at all points between the start position and the end position. Once the inspection crawler 30 has identified the start location, the computer 50 of the inspection system 20 is capable of calculating the exact position of the inspection crawler 30, and thereby of any uncovered discontinuity 28 in the metallic cladding 22, by correlating the measured distance and rotational position provided by the linear and rotation encoders with the start position.

Figure 3:
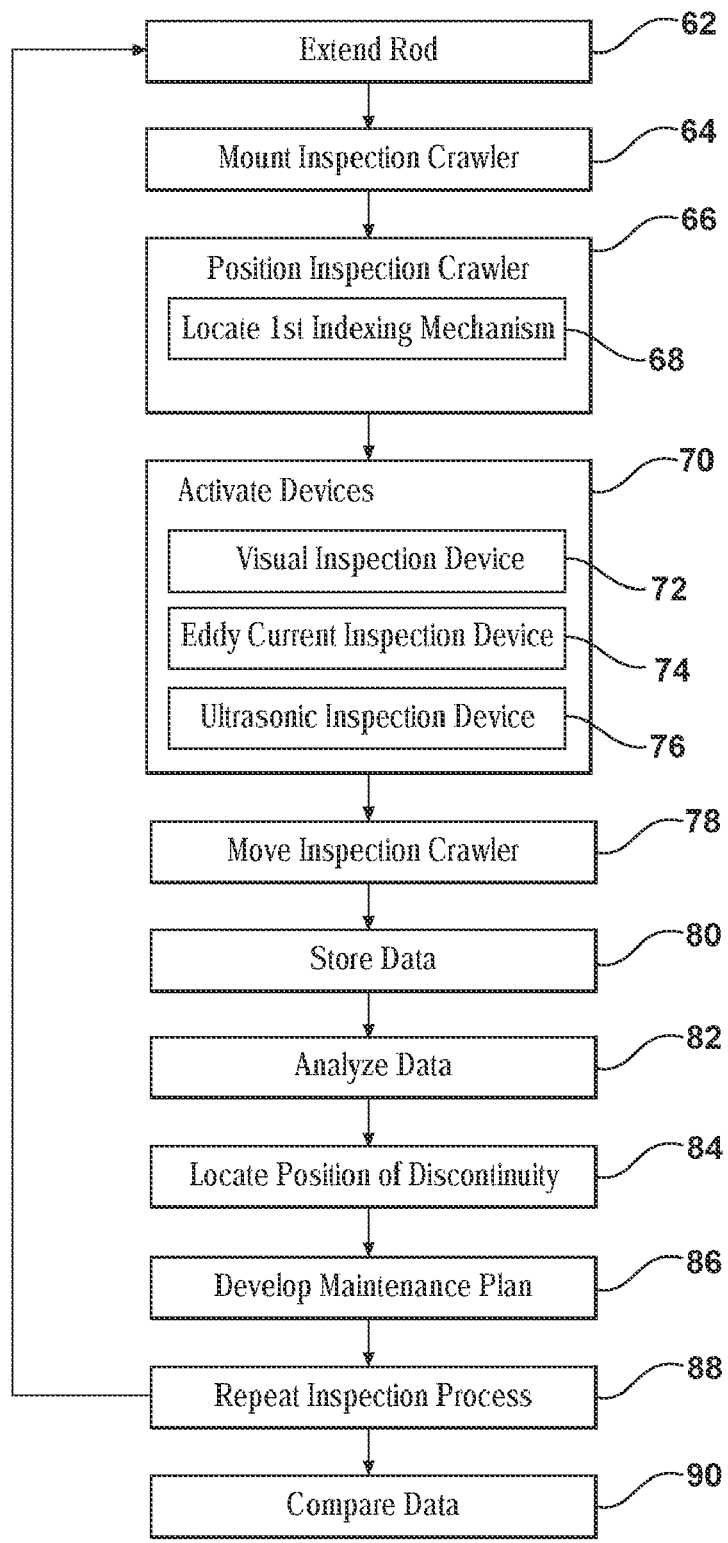
FIG. 3 is a flow chart of a method of maintaining the rod of the hydraulic cylinder.

Referring to FIG. 3, a method of maintaining the rod 24 of the hydraulic cylinder 26 with the inspection crawler 30 is also disclosed. The method includes fully extending the rod 24 from the hydraulic cylinder 26, indicated at 62. This ensures that the metallic cladding 22 over the entire surface of the rod 24 is capable of being inspected.

The method further includes mounting the inspection crawler 30 to the rod 24, indicated at 64. It should be appreciated that the rod 24 is fully extended from the hydraulic cylinder 26 prior to mounting the inspection crawler 30 to the rod 24. The inspection crawler 30 may be mounted to the rod 24 in any suitable manner, so long as the inspection crawler 30 is free to move linearly along the longitudinal axis 32 of the rod 24.

The method further includes positioning the inspection crawler 30 at the start location, indicated at 66. Positioning the inspection crawler 30 at the start position includes locating the first indexing mechanism 58 to identify the start position, indicated at 68. Once the first indexing mechanism 58 is located, the inspection system 20 is capable of orientating itself to the rod 24 to begin the inspection process.

The method further includes activating the visual inspection device 34, the eddy current inspection device 38 and the ultrasonic inspection device 42 to begin collecting data related to the metallic cladding 22, indicated at 70. The visual inspection device 34, the eddy current inspection device 38 and the ultrasonic inspection device 42 are activated by supplying each with a signal or an electrical current to begin operation. For example, the visual inspection device 34 receives a signal activating the camera 36 of the visual inspection device 34 and signaling the camera 36 to begin recording. The eddy current inspection device 38 and the ultrasonic inspection device 42 receive an electrical current to the current transducer 40 and the ultrasonic transducer 44 respectively to begin operation.

The method further comprises videoing the metallic cladding 22 on the rod 24 with the visual inspection device 34 to visually inspect for a discontinuity 28, indicated at 72, detecting a variation in one of a magnetic permeability or an electrical conductivity in the metallic cladding 22 of the rod 24 with the eddy current inspection device 38 to inspect for a discontinuity 28, indicated at 74, and measuring a reflection time of sound waves propagating through the rod 24 and the metallic cladding 22 with the ultrasonic detection device to detect a discontinuity 28, indicated at 76.

The method may include injecting a stream of water onto the rod 24 while transmitting an ultrasonic wave through the stream of water onto the metallic cladding 22 of the rod 24. As described above, the stream of water acts as a couplant for the ultrasonic sound waves.

Alternatively, if one of the rod 24 and/or the inspection crawler 30 is equipped with the Electro Magnetic Acoustic Transducer (EMAT) 48, the method may include emitting an electromagnetic pulse from the EMAT 48 into the rod 24 and converting the electromagnetic pulse into ultrasonic wave within the rod 24 for detection by the ultrasonic transducer 44 of the ultrasonic inspection device 42.

The method further includes moving the inspection crawler 30 linearly along the longitudinal axis 32 of the rod 24 from the start location to the end location, while rotating the visual inspection device 34, the eddy current inspection device 38 and the ultrasonic inspection device 42 around the circumference of the rod 24, indicated at 78. The visual inspection device 34, the eddy current inspection device 38 and the ultrasonic inspection device 42 move linearly and rotate about the periphery of the rod 24 to simultaneously collect data related to the metallic cladding 22 from the visual inspection device 34, the eddy current inspection device 38 and the ultrasonic inspection device 42 along the entire length and circumference of the rod 24 between the start location and the end location.

The method further comprises storing the data collected from the visual inspection device 34, the eddy current inspection device 38 and the ultrasonic inspection device 42 in the memory 54, indicated at 80. The data is stored for analysis at a later time, as well as for comparing the data with data collected at a latter time.

The method further includes analyzing the data collected from the visual inspection device 34, the eddy current inspection device 38 and the ultrasonic inspection device 42 to identify a discontinuity 28 in the metallic cladding 22, indicated at 82. As described above, the discontinuity 28 may include one of porosity in the metallic cladding 22, a cluster porosity in the metallic cladding 22, a crack in the metallic cladding 22, shrinkage of the metallic cladding 22, incomplete fusion of the metallic cladding 22 onto the rod 24, excessive penetration (high dilution) of the metallic cladding 22 into the rod 24 and disbanding of the metallic cladding 22 from the rod 24.

Analyzing the data collected from the visual inspection device 34, the eddy current inspection device 38 and the ultrasonic inspection device 42 to identify a discontinuity 28 in the metallic cladding 22 may further be defined as analyzing the data collected from the visual inspection device 34, the eddy current inspection device 38 and the ultrasonic inspection device 42 to identify a discontinuity 28 in the metallic cladding 22 measuring 0.010 inches or more in a largest dimension of the discontinuity 28. Furthermore, analyzing the data collected from the visual inspection device 34, the eddy current inspection device 38 and the ultrasonic inspection device 42 to identify a discontinuity 28 in the metallic cladding 22 may further be defined as analyzing the data collected from the visual inspection device 34, the eddy current inspection device 38 and the ultrasonic inspection device 42 to measure a thickness of the metallic cladding 22 to the nearest 0.0001 inch.

The method further includes locating a position on the rod 24 of the discontinuity 28 in the metallic cladding 22 based upon the data collected from the visual inspection device 34, the eddy current inspection device 38 and the ultrasonic inspection device 42, indicated at 84. The computer 50 utilizes the linear encoder and/or the radial encoder to identify an exact position on the rod 24, based upon measurements taken from the start location of the data sensed from the visual inspection device 34, the eddy current inspection device 38 and the ultrasonic inspection device 42. If the analysis of the data indicates a discontinuity 28 in the metallic cladding 22, then the location of the discontinuity 28 on the rod 24 is easily ascertainable based upon the location of the data that indicated the discontinuity 28.

Locating a position on the rod 24 of the discontinuity 28 in the metallic cladding 22 may further be defined as locating a circumferential position in degrees from the start location and locating an axial distance along the longitudinal axis 32 of the rod 24 from the start location. The distance along the longitudinal axis 32 may be measured in any units of measurement, such as inches or millimeters. Accordingly, the method assess the current state of fitness of the metallic cladding 22 of the rod 24 to develop the maintenance plan, which permits prediction of when repair must be rendered in order to avoid unexpected and costly downtime associated with failure of the rod 24 and/or the metallic cladding 22.

The method may further include assessing a severity of a detected discontinuity in the metallic cladding to determine a potential to cause the rod to fail. The severity of the discontinuity may be based upon, but is not limited to, a size of the discontinuity, a location on the rod of the discontinuity, a location within the metallic cladding relative to the rod of the discontinuity, the proximity to other detected discontinuities, etc.

The method may further include estimating a life expectancy of the rod based upon the assessed severity of the detected discontinuity. The life expectancy may be estimated based upon empirical data previously collected, or may be estimated by a computer model utilized to simulate the stresses applied to the rod and/or the cladding and the resulting effect on the discontinuity.

The method further includes developing a maintenance plan to address an uncovered discontinuity 28, indicated at 86. Developing the maintenance plan to address the discontinuity 28 may further be defined as planning an action chosen from a group of actions including an immediate action to address the discontinuity 28, a future action to address the discontinuity 28 and no action to address the discontinuity 28. The action may include, but is not limited to, repair of the rod 24 and/or metallic cladding 22, continued monitoring of the discontinuity 28 to gauge any change in the discontinuity 28 over time, or some other protective measure to prevent further expansion of the discontinuity 28 or damage to the rod 24.

The method further includes repeating the inspection process described above, indicated at 88. Specifically, the method includes repeating the mounting of the inspection crawler 30 to the rod 24; repeating the positioning of the inspection crawler 30 at the start location; repeating the activating of the visual inspection device 34, the eddy current inspection device 38 and the ultrasonic inspection device 42 to collect data related to the metallic cladding 22; repeating the moving of the inspection crawler 30 linearly along a longitudinal axis 32 of the rod 24 from the start location to an end location while rotating the visual inspection device 34, the eddy current inspection device 38 and the ultrasonic inspection device 42 around a circumference of the rod 24 to simultaneously collect data related to the metallic cladding 22 from the visual inspection device 34, the eddy current inspection device 38 and the ultrasonic inspection device 42 along the entire length and circumference of the rod 24 between the start location and the end location; and repeating the analyzing of the data collected from the visual inspection device 34, the eddy current inspection device 38 and the ultrasonic inspection device 42 to identify the discontinuity 28 in the metallic cladding 22, on a regular time schedule to collect data related to the metallic cladding 22 at different times. It should be appreciated that the maintenance plan may be evaluated, updated and/or changed to reflect the additional data collected during the repeated processes of the inspection method.

After the above described steps have been repeated, the method may further include comparing the data collected at a first time with the data collected at a second time to gauge change in the metallic cladding 22, indicated at 90. For example, wear of the metallic cladding 22 must be evaluated over time. Additionally, discontinuities 28 that may not pose a problem to the rod 24 at a first time, may over an extended period deteriorate into such a condition that remedial action is required. Accordingly, regularly scheduled inspection of the metallic cladding 22 is required. Preferably, the metallic cladding 22 is inspected every three months. However, it should be appreciated that the inspection frequency may include any time frequency desired. It should also be appreciated that the maintenance plan may also be updated based upon the change in conditions of the metallic cladding detected over time.

A method of inspecting the metallic cladding 22 welded to the rod 24 of the hydraulic cylinder is also disclosed. The method includes positioning the eddy current inspection device 38 adjacent the metallic cladding 22 of the rod 24. The eddy current inspection device 38 may by mounted to the inspection crawler 30 as described above. Alternatively, the eddy current inspection device may by mounted to some other manner of inspection device configured for inspecting the metallic cladding 22, either at the manufacturing location of the rod 24 or in the field, and may include a hand held inspection device.

The method further includes activating the eddy current inspection device 38 to collect data related to the metallic cladding 22. The eddy current inspection device includes a current transducer 40, which conducts a magnetic field or an electrical current through the metallic cladding 22. The method further includes detecting a variation in one of a magnetic permeability or an electrical conductivity in the metallic cladding 22 of the rod 24 to detect a discontinuity in the metallic cladding 22. Accordingly, the variation in the magnetic permeability or the electrical conductivity is the data collected that identifies any discontinuities 28 in the metallic cladding 22.

The method further includes analyzing the data collected from the eddy current inspection device 38 to identify the discontinuity 28 in the metallic cladding 22. Analyzing the data collected from the eddy current inspection device 38 to identify a discontinuity 28 in the metallic cladding 22 may further be defined as analyzing the data collected from the eddy current inspection device 38 to identify a subsurface discontinuity 28 in the metallic cladding 22. Accordingly, the eddy current inspection device 38 is capable of detecting discontinuities 28 in the metallic cladding 22 that are disposed beneath an outer surface of the metallic cladding 22, and are not visible from the outer surface of the metallic cladding 22. As such, the eddy current inspection device 38 provides a more complete inspection of the metallic cladding 22 than the existing technique of liquid penetration, which is incapable of detecting subsurface discontinuities 28.

While the best modes for carrying out the invention have been described in detail, those familiar with the art to which this invention relates will recognize various alternative designs and embodiments for practicing the invention within the scope of the appended claims.

The invention claimed is:

1. A method of maintaining a rod of a hydraulic cylinder with an inspection crawler including a visual inspection device, an eddy current inspection device and an ultrasonic inspection device, wherein the rod includes a metallic cladding welded thereto, the method comprising:
   mounting the inspection crawler to the rod;
   positioning the inspection crawler at a start location;
   activating the visual inspection device, the eddy current inspection device and the ultrasonic inspection device to collect data related to the metallic cladding;
   moving the inspection crawler linearly along a longitudinal axis of the rod from the start location to an end location while rotating the visual inspection device, the eddy current inspection device and the ultrasonic inspection device around a circumference of the rod to simultaneously collect data related to the metallic cladding from the visual inspection device, the eddy current inspection device and the ultrasonic inspection device along the entire length and circumference of the rod between the start location and the end location; and
   analyzing the data collected from the visual inspection device, the eddy current inspection device and the ultrasonic inspection device to identify a discontinuity in the metallic cladding.

2. A method as set forth in claim 1 further comprising locating a position on the rod of the discontinuity in the metallic cladding based upon the data collected from the visual inspection device, the eddy current inspection device and the ultrasonic inspection device.

3. A method as set forth in claim 2 wherein locating a position on the rod of the discontinuity in the metallic cladding is further defined as locating a circumferential position in degrees from the start location and locating an axial distance along the longitudinal axis of the rod from the start location.

4. A method as set forth in claim 1 further comprising assessing a severity of a detected discontinuity in the metallic cladding to determine a potential to cause the rod to fail.

5. A method as set forth in claim 4 further comprising estimating a life expectancy of the rod based upon the assessed severity of the detected discontinuity.

6. A method as set forth in claim 5 further comprising developing a maintenance plan to address the detected discontinuity.

7. A method as set forth in claim 6 wherein developing a maintenance plan to address the detected discontinuity is further defined as planning one of an immediate action to address the detected discontinuity, a future action to address the detected discontinuity and no action to address the detected discontinuity.

8. A method as set forth in claim 1 further comprising repeating the mounting of the inspection crawler to the rod; the positioning of the inspection crawler at the start location; the activating of the visual inspection device, the eddy current inspection device and the ultrasonic inspection device to collect data related to the metallic cladding; the moving of the inspection crawler linearly along a longitudinal axis of the rod from the start location to an end location while rotating the visual inspection device, the eddy current inspection device and the ultrasonic inspection device around a circumference of the rod to simultaneously collect data related to the metallic cladding from the visual inspection device, the eddy current inspection device and the ultrasonic inspection device along the entire length and circumference of the rod between the start location and the end location; and the analyzing of the data collected from the visual inspection device, the eddy current inspection device and the ultrasonic inspection device to identify the discontinuity in the metallic cladding, on a regular time schedule to collect data related to the metallic cladding at different times.

9. A method as set forth in claim 8 further comprising comparing the data collected at a first time with the data collected at a second time to gauge change in the metallic cladding.

10. A method as set forth in claim 1 wherein analyzing the data collected from the visual inspection device, the eddy current inspection device and the ultrasonic inspection device to identify a discontinuity in the metallic cladding is further defined as analyzing the data collected from the visual inspection device, the eddy current inspection device and the ultrasonic inspection device to identify a discontinuity in the metallic cladding measuring 0.010 inches or more in a largest dimension of the discontinuity.

11. A method as set forth in claim 1 wherein analyzing the data collected from the visual inspection device, the eddy current inspection device and the ultrasonic inspection device to identify a discontinuity in the metallic cladding is further defined as analyzing the data collected from the visual inspection device, the eddy current inspection device and the ultrasonic inspection device to measure a thickness of the metallic cladding to the nearest 0.0001 inch.

12. A method as set forth in claim 1 wherein the start location includes a first indexing mechanism and the end location includes a second indexing mechanism, and wherein the method further includes locating the first indexing mechanism to identify the start position.

13. A method as set forth in claim 1 wherein the visual inspection device includes a video camera and the method further comprises videoing the rod to visually inspect for a discontinuity.

14. A method as set forth in claim 1 wherein the eddy current inspection device includes a current transducer and the method further comprises detecting a variation in one of a magnetic permeability or an electrical conductivity in the metallic cladding of the rod.

15. A method as set forth in claim 1 wherein the ultrasonic inspection device includes an ultrasonic transducer and the method further comprises measuring a reflection time of sound waves from within the metallic cladding of the rod.

16. A method as set forth in claim 15 further comprising injecting a stream of water onto the rod while transmitting an ultrasonic wave through the stream of water onto the metallic cladding of the rod.

17. A system for inspecting a metallic cladding on a rod of a hydraulic cylinder, the system comprising:
   an inspection crawler configured for moveable attachment to the rod;
   a visual inspection device mounted to said inspection crawler and configured for visual inspection of the metallic cladding on the rod;
   an eddy current inspection device mounted to said inspection crawler and configured for detecting change in one of a magnetic permeability and an electrical conductivity of the metallic cladding on the rod;
   an ultrasonic inspection device mounted to the inspection crawler and configured for detecting change in sound waves propagated through the metallic cladding on the rod;
   wherein said visual inspection device, said eddy current inspection device and said ultrasonic inspection device are configured for rotation about a circumference of the rod while said inspection crawler moves linearly along a longitudinal axis of the rod to simultaneously collect data related to the metallic cladding from said visual inspection device, said eddy current inspection device and said ultrasonic inspection device along a length and the circumference of the rod.

18. A system as set forth in claim 17 wherein said visual inspection device includes a digital camera, said eddy current inspection device includes a current transducer and said ultrasonic inspection device includes an ultrasonic transducer.

19. A system as set forth in claim 18 further comprising a memory configured for storing data collected from the visual inspection device, the eddy current inspection device and the ultrasonic inspection device.

* * * * *